(12) United States Patent
Blair et al.

(10) Patent No.: US 7,231,390 B2
(45) Date of Patent: Jun. 12, 2007

(54) APPARATUS AND METHOD FOR PROVIDING SEQUENCE DATABASE COMPARISON

(75) Inventors: Douglas M. Blair, Charlottesville, VA (US); John J. Grefenstette, Fairfax Station, VA (US); H. Hadon Nash, Fairfax, VA (US); Dale I. Newfield, Washington, DC (US); Dustin M. Lucien, Washington, DC (US)

(73) Assignee: Parabon Computation, Inc., Reston, VA (US)

( * ) Notice: Subject to any disclaimer, the term of this patent is extended or adjusted under 35 U.S.C. 154(b) by 999 days.

(21) Appl. No.: 09/881,234

(22) Filed: Jun. 14, 2001

(65) Prior Publication Data

US 2001/0053957 A1    Dec. 20, 2001

Related U.S. Application Data

(60) Provisional application No. 60/211,811, filed on Jun. 14, 2000.

(51) Int. Cl.
*G06F 17/30* (2006.01)

(52) U.S. Cl. .................... 707/6; 700/3; 702/19
(58) Field of Classification Search ............ 702/19, 702/20; 700/3; 435/6
See application file for complete search history.

(56) References Cited

U.S. PATENT DOCUMENTS

| | | | |
|---|---|---|---|
| 5,577,249 A | | 11/1996 | Califano |
| 5,706,498 A | * | 1/1998 | Fujimiya et al. ............ 395/606 |
| 5,862,325 A | * | 1/1999 | Reed et al. ................. 709/201 |
| 5,970,500 A | | 10/1999 | Sabatini et al. |
| 6,303,297 B1 | * | 10/2001 | Lincoln et al. ................ 435/6 |

OTHER PUBLICATIONS

Altschul et al. Basic Local Alignment Search Tool, 1990, Journal of Molecular Biology, vol. 215, No. 3, pp. 403-410.*
Anderson et al. Searching DNA databases for similarities to DNA sequences: when is a match significant?, 1998, Bioinformatics, vol. 14, No. 4, pp. 349-356.*
Matsumoto et al., Biological Sequence Compression Algorithms, 2000, Genome Informatics, vol. 11, pp. 43-52.*
"Master/slave" definition, Webopedia, on the world wide web at webopedia.com/TERM/M/master_slave.html, 2001, 2 pages.*

(Continued)

*Primary Examiner*—Carolyn L. Smith
(74) *Attorney, Agent, or Firm*—Roberts Mardula & Wertheim, LLC (57) ABSTRACT

A method and system of comparing a query and a subject database using a distributed computing platform is disclosed. The databases are divided into data elements having a size within a specified range. All data elements and task definitions are sent to a master CPU of a master-slave distributed computing platform, wherein task definitions comprise at least one comparison parameter, at least one executable comparison element, and a query and a subject data element ID/descriptor. Data elements are sent alternately from query and subject data elements. A task definition is sent for each task from the master CPU to one of a plurality of slave CPUs when all parts of a task definition and data elements referenced by the task definition are available at the master CPU. Data elements are then sent to the slave CPUs for performance of the tasks. Task results for each task are returned to a CPU.

23 Claims, 7 Drawing Sheets

OTHER PUBLICATIONS

"Expressed sequence tag" definition, Human Genome Project Information, on the world wide web at ornl.gov/sci/techresources/Human_Genome/glossary/glossary_e.shtml, 2003, 3 pages.*

Smith et al. BCM Search Launcher—An Integrated Interface to Molecular Biology Data Base Search And Analysis Services Available on the World Wide Web. 1996, Genome Research, vol. 6, pp. 454-462.*

"System" definition, Merriam-Webster online dictionary, on the world wide web at m-w.com/cgi-bin/dictionary?book=Dictionary&va=system, 2004, 2 pages.*

"Efficient" definition, online Merriam-Webster dictionary, on the world wide web at m-w.com/cgi-bin/dictionary?book=Dictionary&va=efficient, 2004, 1 page.*

Andreson, Isobel & Brass, Andy, "Searching DNA databases for similarities to DNA sequences: when is a match significant?" Bioinformatics, 1998. pp. 349-365, vol. 14, No. 4, University of Manchester, Manchester, United Kingdom.

Toshiko Matsumoto, Kunihiko Sadakane, & Hiroshi Imai, "Biological Sequence Compression Algorithms" General Informatics, 2000, pp. 43-52, vol. II, Tokyo, Japan.

Karlin, Samuel, et al., "Applications and Statistics for Multiple High-Scoring Segments in Molecular Sequences," Proc. Natl. Acad. Sci. USA, vol. 90, pp. 5873-5877, Jun. 1993.

Altschul, Stephen F., et al., "Gapped BLAST and PSI-BLAST: A New Generation of Protein Database Search Programs," Nucleic Acids Research, vol. 25, No. 17, 1997.

BLAST 2.0 Release Notes (revised May 25, 1998), http://pbil.univ-lyon1.fr/BLAST.description.html.

Varre, Jean-Stephane, et al., "Transformation Distances: A Family of Dissimilarity Measures Based on Movements of Segments," Bioinformatics, vol. 15, No. 3, pp. 194-202, 1999.

Brudno, Michael, et al., "Fast and Sensitive Multiple Alignment of Large Genomic Sequences," BMC Bioinformatics, Dec. 23, 2003.

* cited by examiner

APPARATUS AND METHOD FOR PROVIDING SEQUENCE DATABASE COMPARISON

RELATED APPLICATIONS

This application claims the benefit of U.S. Provisional Application Ser. No. 60/211,811 entitled "Apparatus and Method for Providing Sequence Analysis," filed Jun. 14, 2000 and herein incorporated by reference.

FIELD OF THE INVENTION

The present invention is drawn to an apparatus and method for sequence database comparison. More particularly, it is drawn to a sequence analysis software system for efficient comparison of two large datasets (genome-genome, genome-database, database-database) with both computationally intensive, sensitive methods such as Smith-Waterman, as well as faster heuristic methods such as BLAST, on a large number of processing nodes with limited storage, memory and bandwidth resources.

BACKGROUND OF THE INVENTION

The increasing availability of biological data, computational power, and advanced algorithms in the past decade has transformed the theoretical, academic discipline of Computational Biology into the industrial and technological field of Bioinformatics. Despite advances in general-purpose and specialized computer technology, efficient algorithm design, and commercial investment in bioinformatics technology, analysis of the volume of new data being generated by public efforts and private entities threatens to outstrip current computational resources.

GenBank is a publicly funded database at NIH containing DNA sequences collected from published biological research on various organisms. The amount of sequence in GenBank has grown since 1982 from 680,338 nucleotide base pairs (characters) in 606 sequences to 12.4 billion bases in 11.5 million sequences as of April 2001. GenBank currently is more than doubling in size every year. While this is the growth pattern of the public data, private concerns are also generating enormous amounts of sequence data. Celera Genomics, for instance, has produced at least 6× coverage of two mammalian genomes, *homo sapiens* and *mus musculus*, which must constitute at least 30–40 billion nucleotide bases. Other genomic and pharmaceutical companies are similarly producing data and performing analyses of those data.

In 1965 Gordon Moore, founder of Intel, stated what is now known as Moore's "Law"—that computers will double in speed and capacity every 18 months due to advances in semiconductor technology. This has held essentially true up to now, except that the time has decreased from 18 months to about a year. Even so, the rate of change of computer speeds and capacities is slower than the rate of increase in size of genetic databases.

Advances in algorithms have made some progress in decreasing the cost of computational analysis of genetic data. The Smith-Waterman dynamic programming algorithm, published in 1981, is the most sensitive and well-understood algorithm for comparing genetic sequences. Heuristic methods such as FASTA (1988) and BLAST (1990, 1997) were developed to make these comparisons faster, sacrificing sensitivity for speed. With current semiconductor-based sequential computational technology and the known theoretical algorithmic limitations of sequence comparison, there is little to suggest that any new order-of-magnitude improvements in speed will be made in this area which do not seriously affect the sensitivity of results.

It can be argued that sequence comparison is the single largest current use of computation in bioinformatics. The vast majority of sequence and protein classifications have been made on the basis of comparison with already characterized sequences. Higher level analyses of protein families including position-specific scoring systems, Hidden Markov Models, multiple sequence alignments, and phylogenetic analyses do not necessarily involve sequence comparison per se, but do take the results of database searches as their input.

Programs such as SSEARCH (a software implementation of Smith-Waterman contained in the FASTA package), FASTA and BLAST conform to the one query sequence, one database paradigm. This is essentially an historical artifact of the origins of these programs. In the past, the limiting factor in analysis of a new sequence was not the computation used to compare the sequence to a database, but in the extraction of the sequence itself from an organism. Comparison of a single genetic sequence to a sequence library requires an amount of computation linearly proportional to the size of the library. Computational analysis was simply a minor, final step in the process of studying the newly determined sequence.

In the new era of genomics and proteomics, advances in sequencing technology have changed this equation. Large sequences and entire genomes are becoming available from increasing numbers of organisms. Also, the identification and comparison of individual genes is beginning to give way to the elucidation of entire systems of interrelated genes and gene products common among various classes of organisms. For these reasons, speedy comparison of single sequences to databases, genomes, or proteomes, while still important, is less desirable than sensitive methods for comparison of these datasets to one another in their entirety. This implies that the size of the computations we would like to perform is effectively growing quadratically instead of linearly.

Given that the volume of sequence data is growing faster than improvements in individual computer speeds, vast improvements in the efficiency of sequence comparison algorithms are likely not forthcoming, and the desired amount of computation is growing quadratically, the only clear solution is to throw more computers at the problem. This is indeed what has happened. The Sanger Centre in the UK, a large contributor to the publicly funded Human Genome Project, operates 256 Compaq Alpha CPUs, several 12-processor Compaq Alpha machines, and a cluster of 48 Intel-based Linux boxes. Celera operates an 800–1000 CPU cluster of Compaq Alpha processors. Incyte Genomics operates a 3600 node cluster of Intel-based Linux machines. These organizations continue to upgrade existing equipment and purchase new equipment. Other genomic and pharmaceutical companies and organizations have made or are considering similar purchases. A large percentage of the time spent on these clusters is spent performing BLAST searches.

While these large-scale computational resources have made many of the contemporary advances in genomic research possible, there are significant shortcomings to this approach. The NCBI BLAST (Basic Local Alignment Search Tool) program blastall is probably the most extensively used program in the suite of BLAST programs. It performs the blastn (nucleotide query sequence vs. nucleotide subject database), blastp (amino acid sequence vs. protein subject database), blastx (translated nucleotide sequence vs. protein subject database), tblastn (amino acid sequence vs. translated nucleotide subject database), and tblastx (nucleotide query sequence vs. nucleotide subject database, both translated) algorithms. In comparing one query sequence at a time to a subject database, blastall must scan through all the data in the subject database for each query sequence. The basic BLAST algorithm is fast enough that it spends very little CPU (central processing unit) time with each subject sequence. As a result, the speed with which the algorithm can process subject data significantly exceeds the speed of even the fastest local disks, and far exceeds the speed of most network accessible disks, which are often where large datasets reside.

Thus, if one wishes to maximize the efficiency of a BLAST search, one must ensure that the entire subject dataset resides in main memory within the machine on which the search is being performed. Individual subject databases can range in size from a few thousands of bytes up to (at this writing) almost ten billion bytes (10 gigabytes (GB)). This means that, for the largest searches desired, one must populate EACH machine in a cluster with as much as 10 GB of main memory. Machines that can accommodate this much memory are typically more expensive than commodity PC hardware. Even more dramatically, the cost of the necessary RAM for these machines can often exceed the cost of the machines themselves! Multiply this cost by hundreds or thousands of machines, and it becomes clear that the expense is prohibitive for even the most well-funded organizations. Finally, the size of the genetic databases continues to grow faster than the number of gigabytes of RAM that can be purchased per dollar, even when Moore's Law is taken into account. So, the cost per machine continues to grow.

Several approaches have been taken toward this problem. In the naive method of dividing a database-to-database comparison into multiple subcomparisons, the query database is divided into multiple smaller query sub-databases. Each query sub-database is sent to a separate CPU, as well as the entire subject database, and the comparison is performed. As noted above, this method requires large amounts of RAM to efficiently compare queries to a large subject database. In addition, it also means that for each new CPU employed in the search, the amount of data that must be transferred to that CPU includes the entire subject database. As the number of CPUs employed in the search increases, the total amount of data transferred when initiating a large database-to-database comparison is effectively the number of CPUs times the size of the subject database. This typically saturates the network on which the machines reside, diminishing the usefulness of each new CPU added to the network.

To decrease the memory requirements for each CPU participating in the search, it is possible to divide the subject database into multiple smaller subject sub-databases. This, however, changes the statistical parameters of the search. The primary characteristic of BLAST searches that impinges upon the aforementioned statistical differences is the "size" of the sequence comparison space being searched. Briefly, the comparison search space size is approximately the product of the length of the query sequence multiplied by the sum of the lengths of the sequences in the subject database. Thus, the search space size for the comparison of a query sequence to an entire subject database is different (i.e., larger) than the search space size for the comparison of the same query sequence to a sub-database of that same subject database.

BLAST uses a multi-tiered set of heuristics to successively refine its search results, and the comparison search space size is one of the parameters used to "tune" each of these heuristics. At each successive step of the BLAST heuristic, a decision is made as to which matches to discard, and which matches to subject to further search and refinement. The comparison search space size directly affects the parameters used to make each of these decisions; thus, when the comparison search space size for a search is modified, the results of that search will also differ.

The blastall program does provide two parameters that can be used to attempt to correct for these statistical differences. The "-z" parameter allows the blastall user to specify the effective subject database length used to compute the comparison search space size for each query sequence/subject database comparison, regardless of the actual subject database length. The "-Y" parameter allows the user to specify the comparison search space size, regardless of the length of the query or subject sequences. When dividing a search into multiple sub-searches, these two parameters override the actual size of the search space in each sub-search, replacing the actual sub-search space size with the virtual "entire" search space size.

Unfortunately, due to bugs and anomalies in the NCBI BLAST version 2.0.14 suite of programs which is in wide use today, the use of the -z and -Y parameters does not allow the user to produce identical results with one large search and multiple smaller sub-searches. Anecdotal accounts from users of blastall suggest that it is unclear that the comparison search space size imposed upon blastall by the use of these flags consistently affects the heuristic parameters of the search. Although there is no theoretical reason why exactly identical results cannot be obtained, it is difficult to demonstrate conclusively whether use of the -z or -Y parameters allows the different searches to select or discard identical matches at each step of the search. Without detailing all known bugs and anomalies in blastall 2.0.14 here, however, it is sufficient to explain one well-understood anomaly to effectively demonstrate that the results will not be identical.

The NCBI BLAST suite of programs includes a program called formatdb that converts a text-based sequence database into a specialized format. The blastall program requires such a formatted database for the subject database when it performs a search. The "blastn" algorithm implemented in blastall, for instance, requires a formatted nucleotide database for the subject database. In order to reduce the size of the database, and as an optimization for speedier comparison of nucleotide sequence data, formatdb converts each ASCII character representing a single nucleotide (e.g. 'A', 'C', 'G', 'T', 'U', 'a', 'c', etc.) into a two bit value representing one of the four standard nucleotides, A, C, G or T(U). These are then packed four at a time into 8-bit bytes in a packed database file.

As a result of imperfect sequence reads from automated nucleotide sequencing equipment, incomplete or inconsistent sequence assembly, reverse translation of amino acid sequences, or other sequence generation errors or inconsistencies, the exact standard nucleotide at each position of a sequence may not be known. In this case, the text file may contain characters other than upper or lower case A, C, G, T, or U. These characters are known as ambiguity characters, and represent the possible characters at a given position in a sequence. For instance, if it is known that a given nucleotide is either an 'A' or a 'C', but not which one, the character at that position may be expressed as an 'M'. If no information about a nucleotide's identity is known, the character at that position may be expressed as an 'N'.

Including the ambiguity characters, then, there are sixteen possible logical nucleotide representations for each nucleotide in a sequence. This exceeds the 4 possibilities that can be encoded in the two bits allocated to each nucleotide by formatdb. In order to get around this, formatdb replaces the ambiguous nucleotide with one of the four standard nucleotides, randomly chosen. The resulting packed database of standard nucleotides is then used in the actual search. The original ambiguous nucleotide characters are restored only when the final results and sequence alignments are generated.

In order to subdivide a large subject database into many smaller subject sub-databases for use in multiple blastall runs with the -z or -Y parameters, each of the sub-databases must first be processed with formatdb. The following observation is the crux of the current explanation about one cause of differences in search results: for each run of formatdb, the standard nucleotides which replace the ambiguity characters are chosen using a random number generator which depends, in part, on the position of the ambiguity character in the database. Thus, the standard nucleotides chosen at each ambiguous position of a sub-database will be largely DIFFERENT than the standard nucleotides chosen for the corresponding position in the unified database from which the sub-database was extracted. As a result, the significant matches found by the many sub-comparisons are NOT equivalent to the significant matches found when comparing a query sequence to the entire subject database in one unified blastall run. This is especially true and vexing when the subject database(s) contain many ambiguity characters.

Setting aside for a moment the previously mentioned pitfalls (i.e. resource limitations such as RAM, local disk space, and bandwidth interconnect for each CPU, inconsistency of results from subdivided searches, etc.) assume that one may use the blastall program with acceptable efficiency and accuracy, either in the naive manner, or with the -z and -Y arguments. How will the program be distributed to the individual CPUs? Are the CPUs heterogeneous? Will executables be needed for multiple architectures? How will the databases be subdivided, have formatdb run on them, and be distributed to all the CPUs? What happens if one of the subcomparisons fails? How will all the results be collected and reintegrated in a useful and efficient manner?

Currently, there is no single answer to any of these questions. Organizations are left with a range of choices—from developing their own solutions to these problems, to purchasing a commercial cluster load-balancing system, which will typically still require a significant investment in configuration and troubleshooting. While many script-based tools, such as the BioPerl toolkit, are available to perform tasks such as parsing of BLAST output, there is still a great deal of labor involved in building, deploying, and debugging user-friendly software to manage large BLAST jobs on a cluster of machines. Even commercial systems do not necessarily guarantee robustness of the programs they are running. If the blastall program fails on one of the CPUs, for whatever reason, the software managing the job needs to be told explicitly how to handle the disconnect. These are nontrivial issues that require significant manpower investment.

Assuming that these problems of robustness have been dealt with in a distributed BLAST solution using blastall, there still remains the matter of efficiency. The blastall program generates large quantities of ASCII text, which must somehow find its way from each CPU running the program to a storage unit, usually a large network mounted RAID system. The information content of the results, however, is significantly less than the size of the text generated. Few systems compress the results for transmission across the network, however, instead usually writing directly to the remote disk. Newer versions of NCBI BLAST (2.1.X) support generation of XML—encoded results, which may improve these bandwidth issues somewhat, but many production environments have yet to adopt this newer format. Computational efficiency is important as well as storage and bandwidth efficiency. Perl programs for managing and parsing these large quantities of output can be an order of magnitude slower than their (probably nonexistent) equivalent in a compiled language such as C. For these reasons, a more tightly integrated software architecture is highly desirable to maximize the efficiency of very large sequence database comparison

BRIEF SUMMARY OF THE INVENTION

It is an object of the present invention to provide the design, implementation, testing and benchmarking of a new distributed system for performing genetic sequence comparison and statistical analysis. The present invention exhibits a new design and implements a new system that overcomes the aforementioned limitations. In particular, it enables very large, sensitive, and efficient database-to-database comparisons on a heretofore impossible number of CPUs with modest RAM, local disk, and bandwidth interconnection resources. This lays the groundwork for the most precise and exhaustive characterization of all known genetic sequence data yet performed.

The invention solves the problem of performing many individual queries against a subject database on many machines, each containing significantly less random access memory (RAM) than would contain the subject database. The invention also greatly reduces the data transmission requirements for performing the entire comparison on these many machines.

It is an object of the present invention to provide a method and apparatus to perform database comparisons.

It is a further object of the present invention to perform very large-scale database-to-database genetic sequence database comparisons, up to, including, and beyond Human Genome vs. GenBank-sized searches.

It is yet another object of the present invention to perform these database-to-database comparisons using both computationally intensive, exact methods such as Smith-Waterman, as well as heuristic methods such as BLAST.

It is yet another object of the present invention to perform these database-to-database comparisons on a very large number of CPUs with potentially modest RAM, disk space, and bandwidth interconnection resources.

It is yet another object of the present invention to perform these database-to-database comparisons on a very large number of CPUs in such a way as to exactly reproduce the equivalent non-parallelized computation result.

It is yet another object of the present invention to produce results from these database-to-database comparisons in a seamless, integrated fashion, and to provide strong guarantees for completion of these large, distributed jobs.

It is a further object of the invention to provide a means for dividing both query and subject databases, not just query databases.

It is another object of the invention to provide "square" tasks to maximize the compute/data ratio for each task and make compression worthwhile.

It is a further object of the invention to provide a means to maximize the compute/data ratio for a given number of computing nodes.

It is a further object of the invention to provide a "tunable" compute/data ratio for algorithms with differing computational intensity by allowing data element size to be modified.

It is yet another object of the invention to provide an improved order of task launch by alternating transmission of data segments to the master CPU from each database.

It is a further object of the invention to provide a means to perform both BLAST (NCBI blastall 2.0.14) and Smith-Waterman analysis.

It is a further object of the invention to provide a means to perform all five types of blastall analysis, as well as analogous versions of Smith-Waterman analysis.

It is another object of the invention to provide an integrated (i.e. non-ad hoc) system for scatter/gather of tasks/results.

It is another object of the invention to provide an integrated division of data into overlapping tasks and sequences.

It is another object of the invention to provide a mechanism for splitting and overlapping of data between tasks/data elements for handling long sequences.

It is another object of the invention to provide a mechanism for splitting and overlapping of data within a data element to provide for the maximum recommended blast sequence size and identification of multiple results/sequence pairs with Smith-Waterman analysis.

It is yet another object of the invention to provide a randomization of query and subject databases so as to distribute results for multiple related sequences across many tasks, reducing extreme variance in computation time and results size between tasks so as to provide fewer late or truncated task results.

It is another object of the invention to provide a means for novel integration of results processing for many queries.

It is another object of the invention to provide amortization of database access over task result processing time.

It is another object of the invention to provide increased locality of reference for task results when generating output.

It is yet another object of the invention to provide for the unified generation of query 1/results, query 2/results, etc.

It is another object of the invention to provide an exact reproduction of NCBI blastall 2.0.14 results, when sequences are not cut.

It is another object of the invention to dramatically reduce the amount of RAM, disk space, and connection bandwidth necessary on each slave CPU.

It is another object of the invention to dramatically reduce the total data transmitted to/from slave CPUs.

It is another object of the invention to reduce the total cost of equipment and/or increases work with the same resources.

It is another object of the invention to provide a database comparison process that is scalable to thousands of CPUs.

It is another object of the invention to extend the useful life of existing hardware since machines with modest capabilities can continue to contribute computation in a meaningful way.

DETAILED DESCRIPTION OF THE INVENTION

Invention performs comparison of two databases, a query database, and subject database, searching for similar database entries according to user-defined similarity criteria. Although disclosed primarily for genomic and proteomic analysis, it is understood that the present invention is not meant to be so limited, as it is useful for comparison of any other types of suitably-sized data strings.

Figure 5:
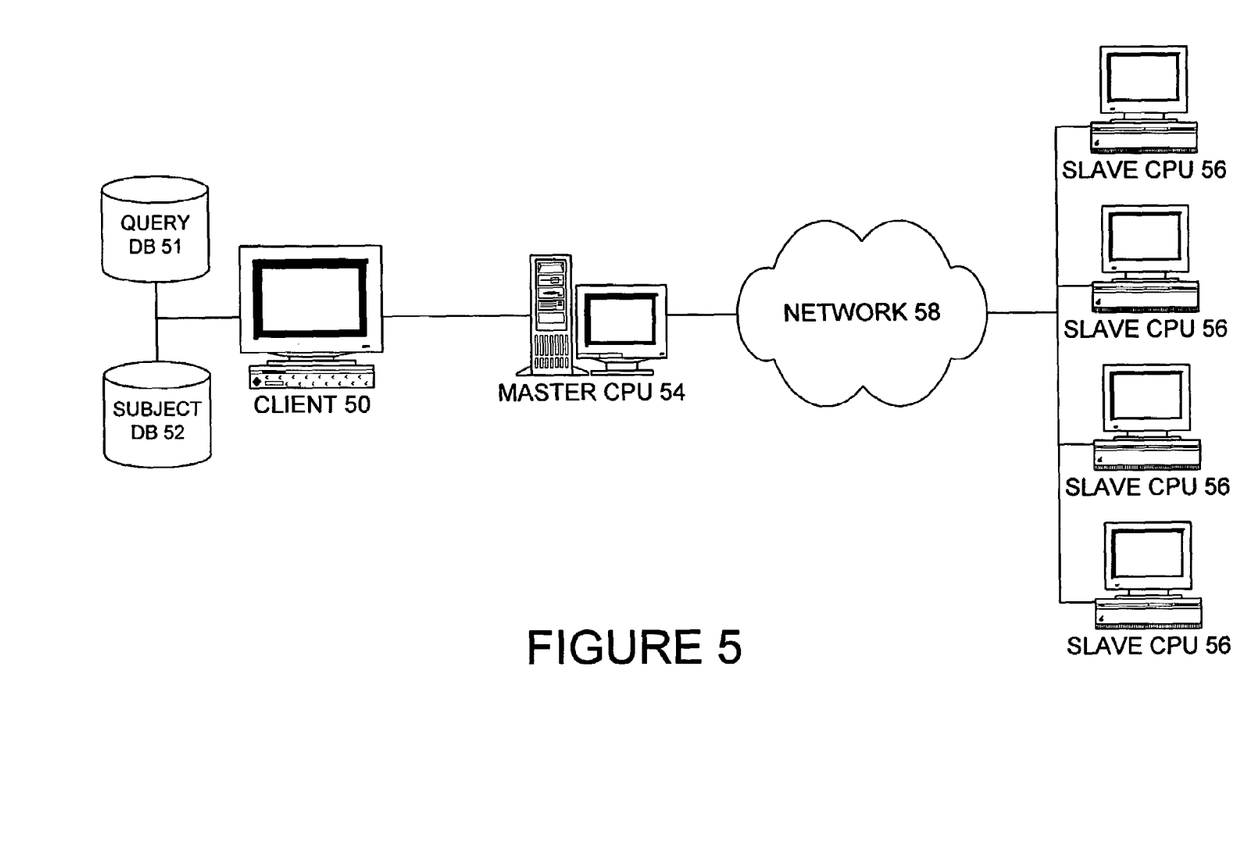
FIG. 5 illustrates a typical system for implementing the present invention.

The apparatus, as illustrated diagrammatically in FIG. 5, comprises a client computer or system 50 with access to the query and subject databases 51, 52 in communication with a master CPU 54. The master CPU 54 is in communication, at least intermittently, with a plurality of slave CPUs 56 over suitable means, such as a network 58 that could comprise a LAN, WAN, the Internet, etc. In a preferred embodiment, client computer 50 employs Prospector™ software from Parabon™ Computation of 3930 Walnut Street, Suite 100, Fairfax, Va. 22030-4738. Likewise, the slave CPUs 56 preferably employ client software in the form of Parabon's Frontier® distributed computing client software and the master CPU 54 employs Parabon's central task server software all as disclosed in co-pending application Ser. No. 09/648,986, filed Aug. 28, 2000, and incorporated herein by reference in its entirety.

Although illustrated as separate and single computers, client system 50 and master CPU 54 could also each consist of plural computers, be co-located, or even be a single computer; they are shown as separate, single computers for clarity.

The basic method of the present invention is outlined in the 11 numbered sections below:

1. If either the query or subject database set (dataset) contains related sequences in a contiguous arrangement, randomize the order of sequences in the two databases.

2. Run NCBI formatdb 2.0.14 on both the query and subject databases. This allows the invention to use exactly the same ambiguity substitutions, etc., as NCBI blastall.

3. Divide each dataset into approximately equal-sized virtual pieces, hereinafter referred to as data elements:
    A. Choose data element size based on computational intensity of comparison algorithm (BLAST or Smith-Waterman), desired ratio of computation time to data transmitted, and available storage and RAM on slave CPUs.

B. The randomization of sequences can be done as in step 1, above, or within Prospector™ itself. When done by Parabon's Prospector™, if either the query or subject database set contains related sequences in a contiguous arrangement, randomize the order of sequences among the data elements by assigning each query or subject database sequence to a data element with the least size.

C. If individual database entries are larger than the desired data element size:
  i. divide database entry into two smaller, overlapping pieces in two data elements, or
  ii. choose to put large database entry into its own oversized data element.

D. If individual database entries within a data element are larger than the maximum desired datasize:
  i. divide individual database entries within a data element into multiple entries of desired maximum length with overlap. Overlap of 50% ensures that no query/subject match less than the overlap length will be missed.

E. Strip all metadata from database entries. Context may be reconstructed with location information placed into data elements.

F. Pack data into efficient structure, e.g. 2 bits per nucleotide with appropriate encoding, 5 bits per amino acid residue with appropriate encoding, etc.

G. Create index for data and pack index and data into uncompressed data element structure.

H. Compress data into compressed data element structure with standard redundancy reduction data compression method, e.g. gzip, pkzip, etc.

4. Determine number of tasks for entire dataset-to-dataset (e.g., database-to database) comparison:
  A. Determine number of data elements $n_N$ created from query database.
  B. Determine number of data elements $n_M$ created from subject database.
  C. Number of tasks is equal to $n_N \times n_M$.

5. Send comparison parameters, executable elements, data elements, and task definitions to master CPU of master-slave computation nodes:
  A. Send comparison parameters to master CPU, e.g. BLOSUM62 comparison matrix, gap penalties for sequence comparison, or other appropriate comparison parameters for other kinds of comparisons.
  B. Send element to master CPU containing executable code for comparison to be performed.
  C. Data elements, task definitions, and ready tasks:
    i. Definition: Data element—compressed package of data as defined in step 1, above, with ID/descriptor.
    ii. Definition: Task definition—comparison parameters, executable element, query data element ID/descriptor, and subject data element ID/descriptor.
    iii. Definition: Ready task—a task is "ready" when its task definition and all parts referred to by its task definition are resident and complete on the master CPU. A ready task may be distributed by the master CPU to a slave CPU. A task that is not yet ready may not be distributed by the master CPU to a slave CPU.
  D. Alternate transmission of query and subject data elements to the master CPU; Send all task definitions for tasks that are otherwise complete at the earliest opportunity:
    i. Send first data element from query database to master CPU.
    ii. Send first data element from subject database to master CPU.
    iii. All necessary elements for task 0 are now at the master CPU. Send the task definition for task 0.
    v. Send second data element from query database to master CPU.
    vi. All necessary elements for task 1 are now at the master CPU. Send the task definition for task 1.
    vii. Send second data element from subject database to master CPU.
    viii. All necessary elements for tasks 2 and 3 are now at the master CPU. Send the task definitions for tasks 2 and 3.
    ix. Continue transmission of data elements to the master CPU, alternating between data elements from query and subject databases; Following transmission of a data element to the master CPU, transmit all task definitions for tasks which are now otherwise complete.
    x. If there are fewer data elements from one of the two databases, continue sending the remaining data elements from the more numerous of the two to the master CPU as in step vi., followed by all task definitions for tasks which are now otherwise complete.

6. Transmit comparison parameters, executable element, query data element and subject data element specified by each task definition to one slave CPU per task definition; The master CPU may transmit these data necessary for computation of a task to a slave CPU as soon as the task is ready as defined in 5.C.iii., above.

7. Perform tasks on slave CPUs using software program embodied in transmitted executable element; For each task:
  A. Uncompress and unpack the data from the query and subject data elements.
  B. Loop through the query sequences from the query data element, performing setup, preprocessing, and table generation for each row of comparisons, as necessary for the given comparison algorithm, e.g. 20-row amino acid table for Smith-Waterman, 6 translated word hit lookup tables for blastx, low-complexity filtering (dust, seg), etc.; For each query sequence:
    i. Loop through the subject sequences from the subject data element; For each query and subject sequence pair:
      a. Perform comparison of query and subject sequence with appropriate sequence comparison algorithm or algorithms contained in the executable, using the transmitted sequence comparison parameters.
      b. Choose to keep or discard result based on user-defined significance criteria, also contained in the transmitted sequence comparison parameters. This may include criteria that take into account characteristics of the entire subject and/or query database.
  C. For each result that meets the user-defined significance criteria, store minimal information that will allow the efficient and complete reconstruction of the significant match on the client CPU:
    i. index information for query and subject sequences
    ii. bounds information for start and stop of pertinent query and subject sub sequences
    iii. data that quantify the fulfillment of the significance criteria for the significant match, e.g. Smith-Waterman or BLAST alignment raw scores, bit scores and E( )-values, etc.

iv. an efficiently encoded representation of the alignment between the bounds specified in ii., above, corresponding to the high-scoring segment pair.
v. For BLAST specifically, store the seed point and sum-set membership for each alignment
D. When all query/subject pairs have been compared, compress the stored results and return them from the slave CPU to the master CPU, and thereby to the client CPU for results processing.

8. After all tasks have been launched from the client to the master (and preferably, but not necessarily while tasks are being performed), generate query report files, one for each sequence in the query database.
A. Create directories for each 1000 sequences in the query database. (They are named Queries.000–999, Queries.1000–1999, etc.)
B. Create one file in the appropriate directory for each sequence in the query database. (Named 000.query, 001.query, etc.)
C. Put the query data and metadata for each query sequence at the beginning of each file.

9. As the set of task results is returned from each task to the client CPU, process each set of task results on the client CPU:
A. Retrieve the query and subject sequence data and metadata corresponding to the task that the results came from.
B. For each significant result in the task results:
i. retrieve the metadata for the subject sequence, the partial subject sequence data corresponding to the subject bounds of the significant alignment result, and the other results data as specified in 7.C., above
ii. append these data to the query results file corresponding to the query sequence 10. When all (i.e. $n_M$) task results have been returned from a given "row" of tasks, each query file corresponding to query sequences from that row of tasks will contain all information necessary to reproduce a report identical to the BLAST report generated by blastall (and a BLAST-like report for Smith-Waterman). For each complete row of tasks:
A. For each query result file:
i. retrieve the query sequence and metadata.
ii. sort the significant results by expectation value (taking the sum-set expectation value into account for results which are part of a sum-set—BLAST only)
iii. remove any identical/redundant results due to overlapping of data elements/sequences.
iv. generate text output for each query sequence identical to the output generated by a blastall run of the query sequence against the subject database.

11. When all results from all rows of tasks have been processed, all results may be concatenated together automatically (or manually, if desired) to produce a text results file identical to the output of a single blastall run of the query database vs. the subject database.

Figure 1A:
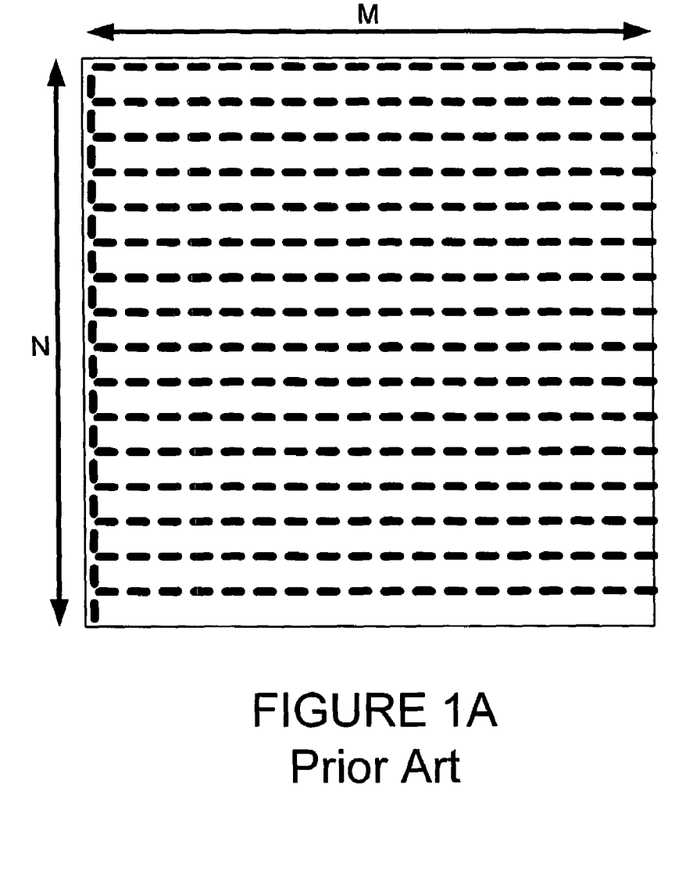
FIG. 1A illustrates in a graphical manner the linear scaling of data transmitted with the number of processors k in prior art parallel processing of database comparisons.
Figure 1B:
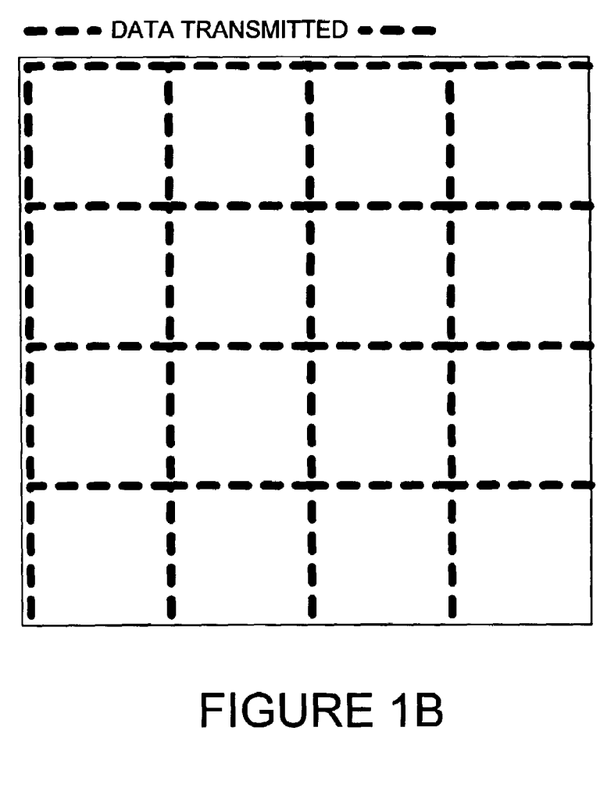
FIG. 1B illustrates in a graphical manner the $k^{1/2}$ scaling of data transmitted with the number of processors k in database comparisons in accordance with the present invention.

The parallel processing architecture and method of the present invention has many advantages over the prior art. FIGS. 1A and 1B illustrate, in a graphical manner, these differences between the prior art and the present invention in comparing databases M and N with k computers. The prior art of FIG. 1A shows the linear scaling of data transmitted with the number of processors k when comparing database M with a segment of database N per computer k. In this arrangement, data transmitted per computer k is M+(N/k), which linearly decreases towards M, a very large amount of data, for a total amount of data is (k×M)+N, which linearly increases as k increases.

The present invention, illustrated in FIG. 1B, illustrates the improvements. In the present architecture, the data transmitted per computer k is $(M+N)/k^{1/2}$ and the total data transmitted is $(M+N) \times k^{1/2}$. This non-linear scaling to $k^{1/2}$ significantly reduces any penalty to using a very great number of processing computers.

Also, the RAM and storage requirements per CPU can be related to the amount of data transmitted, since it will all go into RAM to perform the comparison analysis. The necessary RAM and storage for a prior art machine of FIG. 1A is proportional to M+N/k, and the necessary RAM and storage for a machine of the present invention as represented by FIG. 1B is proportional to $(M+N)/k^{1/2}$. For k>=4, these lower RAM requirements are an improvement, and for k>>4 these are vast improvements.

Figures 2A, 2C:
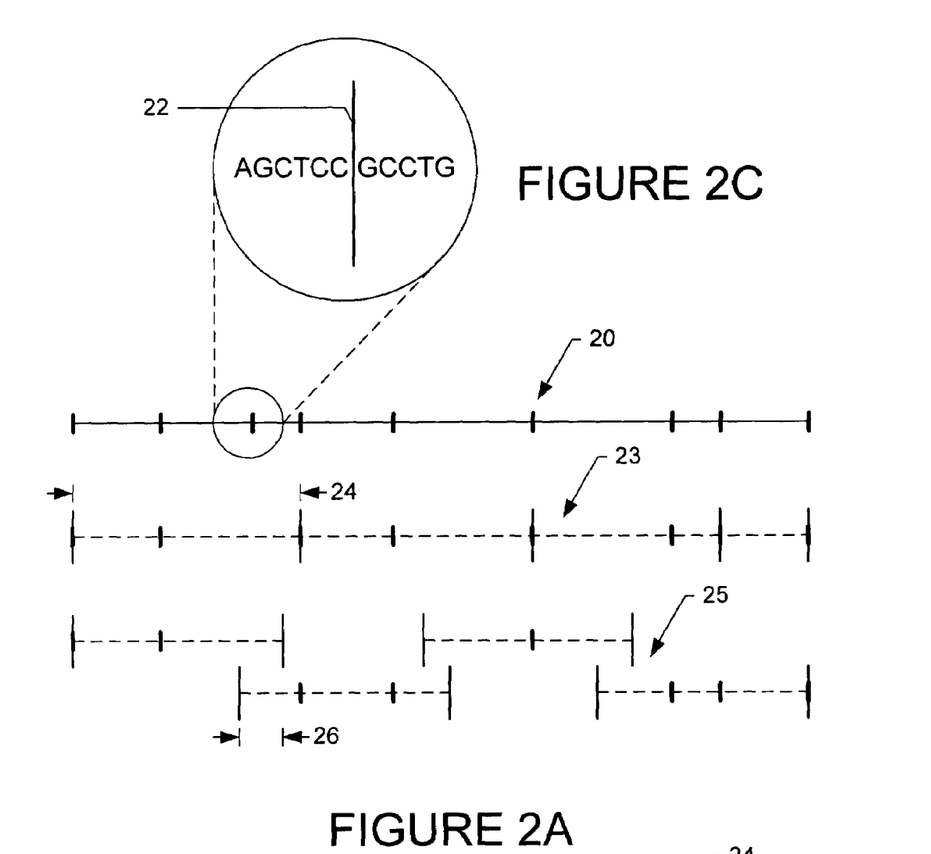
FIGS. 2A–C illustrate the relationship of the data element of the present invention to the database sequences.
Figure 2B:
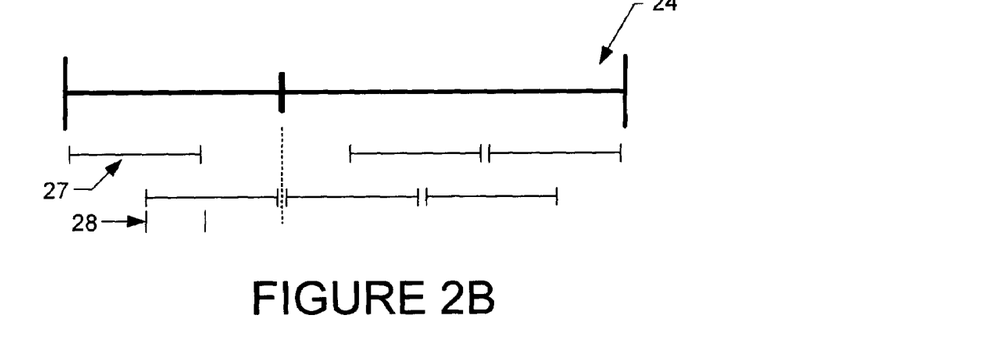

FIGS. 2A–B illustrate the relationship of the data element of the present invention to the database sequences. FIG. 2A shows one of the two (query or subject) databases 20 composed of some number of sequences having boundaries 22, as illustrated in enlarged view FIG. 2C. These sequences are grouped into sets of sequences, each set comprising a data element 24. Data elements are of approximately a user-defined desired data size. If the user chooses that no sequences will be split between data elements, each sequence is placed in its entirety into one data element and the data elements do not overlap, as illustrated at 23. If the user chooses otherwise, as in individual sequences may be "split" between data elements, with a redundant portion of the sequence, or overlap 26, being placed in two data elements, as illustrated by the overlapping data elements at 25.

FIG. 2B shows the disposition of sequences within a data element 24 when operated on by the slave CPU. For purposes of effective and efficient operation of sequence comparison algorithms, sequences may be "chopped" into overlapping subsequences 27. The length of the subsequences 27, as well as the length of the overlap 28, is user-defined. These subsequences 27 are the actual units of sequence that are compared.

The degenerate case of "no splitting (or overlap) between data elements, and no chopping of sequences into subsequences (with overlap)" causes the subsequences which are the actual units of sequence which are compared to be exactly the original sequences from the library.

Figure 3:
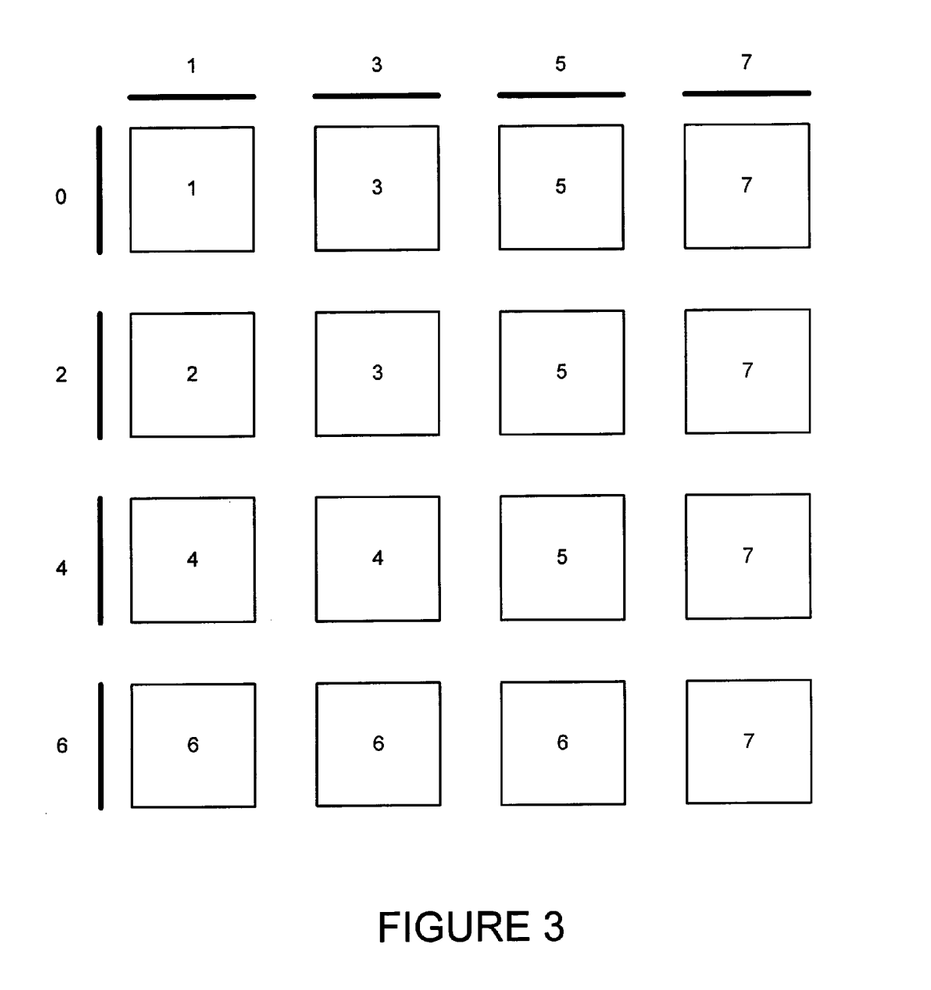
FIG. 3 illustrates the amortization of tasks that are ready to be worked on as alternating data elements from query and subject databases arrive at the master CPU in accordance with the present invention

FIG. 3 illustrates the amortization of tasks that are ready to be worked on as alternating data elements from query and subject databases arrive at the master CPU in accordance with the present invention. In order to maximize throughput, it is desirable to maximize the number of tasks that become ready after the transmission of a data element. For a given (even) number 2n of data elements, the largest number of tasks that might be made ready is $n^2$, which must be arranged in a square. Thus, for every two new data elements added to a job with $n^2$ tasks, the new most efficient conformation is a job of $(n+1)^2$ tasks. This order of data element transmission and task definition assignment achieves the desired theoretical maximum number of ready tasks per transmitted data element.

In the illustrated example, data element 0 from the query dataset arrives first at the master CPU. Then data element 1 from the subject dataset arrives and the single task 1 is "ready." Next, data element 2 from the query dataset arrives at the master CPU and task 2 is "ready." Then data element 3 from the subject dataset arrives and two tasks 3 are "ready." Data element 4 from the query dataset arrives at the master CPU and the two tasks 4 are "ready." Then data element 5 from the subject dataset arrives at the master CPU and the three tasks 5 are "ready." Then data element 6 from the query dataset arrives at the master CPU and the three tasks 6 are "ready." Data element 7 from the subject dataset arrives at the master CPU and the four tasks 7 are "ready," etc., etc. If there are fewer data elements from one of the two databases, the client continues sending the remaining data elements from the more numerous of the two to the master CPU, followed by all task definitions for tasks which are now otherwise complete.

Figure 4A:
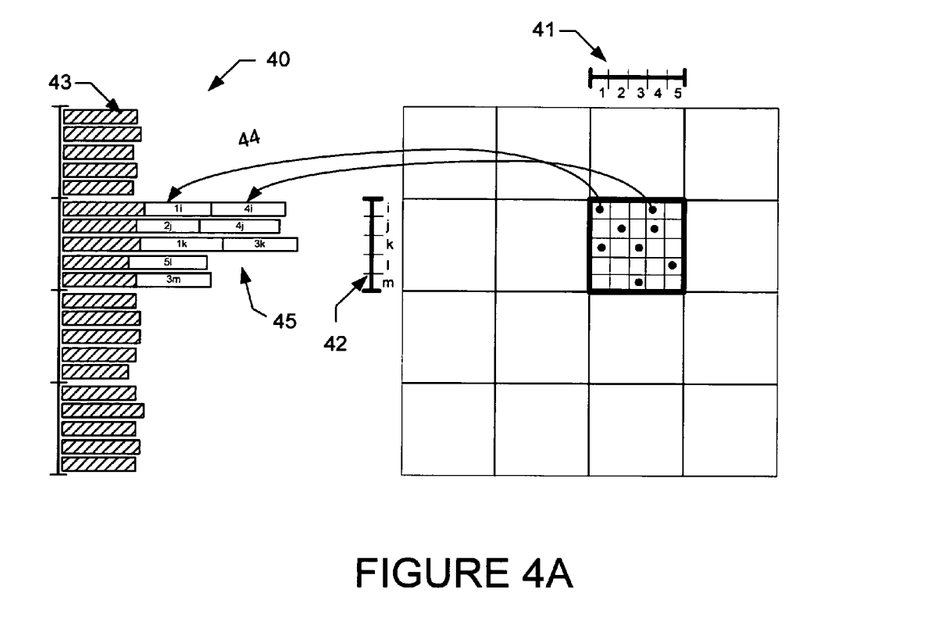
FIGS. 4A illustrates the formation of a partial results file and 4B illustrates the query results file processing into BLAST-type output.
Figure 4B:
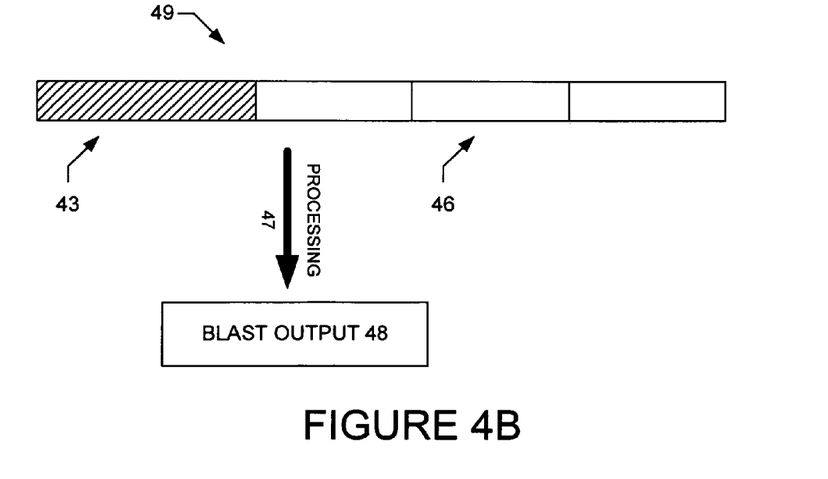

FIGS. 4A and 4B illustrate the client-side handling and processing of results returned by the master CPU from tasks performed on the slave CPUs. For each query sequence, a query result file 49 is created. FIG. 4A illustrates a partial results file 40 for a query sequence in which a first task result for data elements 42/41 have been received. The query sequence and metadata 43 are placed at the beginning of each query result file. Each set of results from a task, such as that shown comparing query data element 42 with subject data element 41, contains some number of query sequence (e.g., "i")/subject sequence (e.g., "1", "4") matches 44 that satisfied the user-defined significance criteria. Each of these results 45 is appended to the query result file corresponding to the query sequence of the query/subject sequence pair, along with the subject subsequence data corresponding to the significant match subject sequence bounds. Although the task illustrated shows a 5×5 sequence comparison, this is not meant as a limitation.

FIG. 4B illustrates the processing of results for a given query sequence. When all task results 46 that contribute significant query/subject sequence pairs for this query sequence have been completed by tasks, received by the client, and appended to the query results file 49, the query results file is processed 47 to produce BLAST output 48. The results are sorted by significance, and a text report for the query sequence in question is produced. For BLAST, the output is identical to NCBI blastall 2.0.14, and for Smith-Waterman, the text report is a BLAST-like report.

Figure 6:
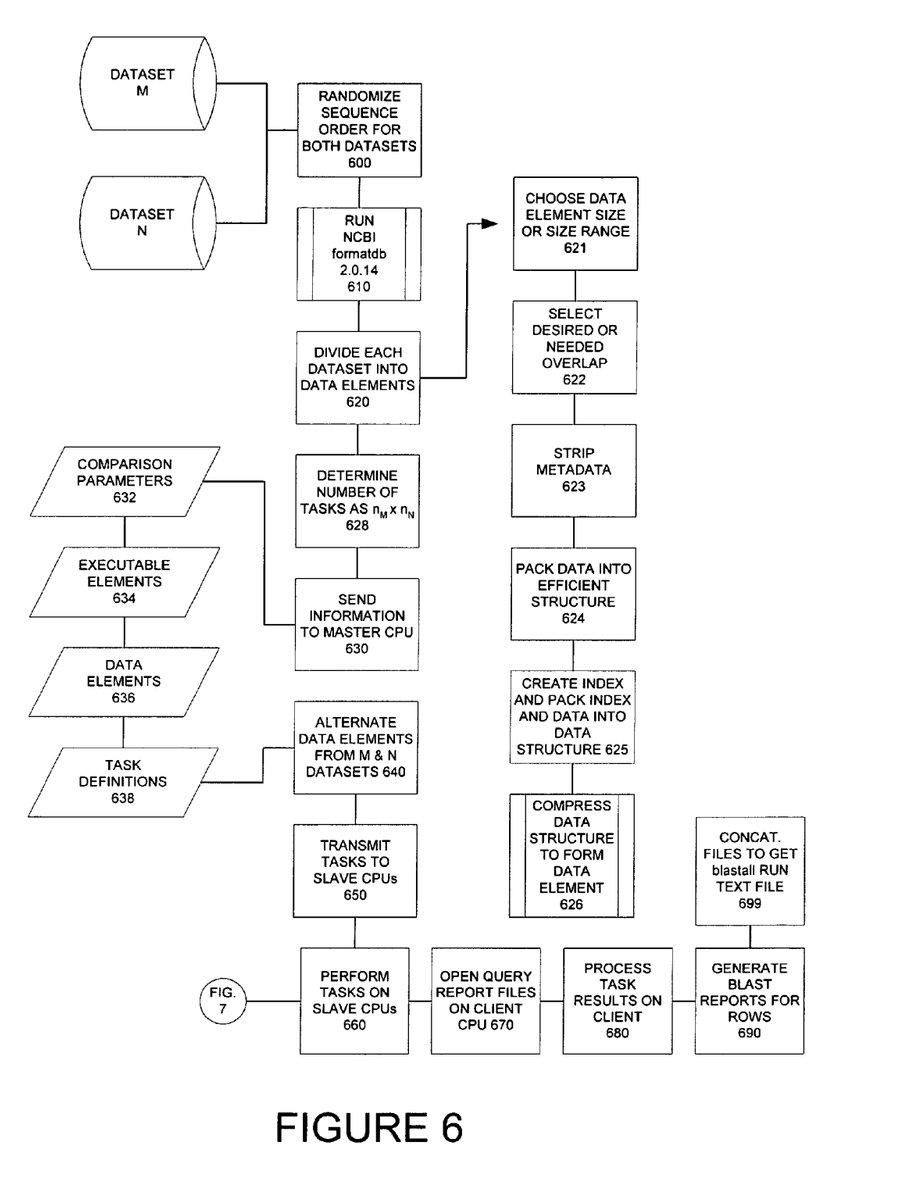
FIG. 6 illustrates a flow chart of the basic process of the present invention.

As illustrated in the flow chart of FIG. 6, if either the query or subject database set M or N contains related sequences in a contiguous arrangement, it is desirable to randomize the order 600 of sequences in the two databases. Next, NCBI formatdb 2.0.14 is run 610 on both the query and subject databases. This allows the invention to use exactly the same ambiguity substitutions, etc., as NCBI blastall. Each dataset M and N is divided into approximately equal-sized data elements 620, wherein data element size is chosen 621 based on factors such as computational intensity of comparison algorithm (BLAST or Smith-Waterman), desired ratio of computation time to data transmitted, and available storage and RAM on slave CPUs.

If individual database entries are larger than the desired data element size, the entry is divided into two smaller, overlapping pieces 622 in two data elements, or the entry is put into its own oversized data element. If individual database entries within a data element are larger than the maximum desired datasize, the individual database entries within a data element are divided into multiple entries of desired maximum length with overlap. Overlap of 50% ensures that no query/subject match that is less than the overlap length will be missed.

All metadata is then stripped 623 from database entries. Context may be reconstructed with location information placed into data elements. Data is then packed into an efficient structure 624, e.g. 2 bits per nucleotide with appropriate encoding, 5 bits per amino acid residue with appropriate encoding, etc. An index is created for the data and the index and data are packed into an uncompressed data element structure 625. Data is then compressed into a compressed data element structure 626 with a standard redundancy reduction data compression method, e.g. gzip, pkzip, etc.

The next step is to determine the number of tasks 628 for the entire dataset-to-dataset (database-to-database) comparison by determining the number of data elements $n_M$ created from the subject database M, determining the number of data elements $n_N$ created from the query database N to find the number of tasks is equal to $n_M \times n_N$.

Comparison parameters 632, executable element or elements 634, data elements 636, and task definitions 638 are then sent to the master CPU of the master-slave computation nodes. Comparison parameters 632 that are sent to the master CPU are parameters such as, but not limited to, BLOSUM62 comparison matrix and gap penalties for sequence comparison. The executable element 634 comprises the code for the comparison to be performed. These will typically be the comparison algorithms written, for example, in JAVA.

The transmission of the data elements 636 and task definitions 638 is done alternately 640 (as per FIG. 3) to allow efficient transmission of ready tasks since a task is "ready" when its task definition 638 and all parts referred to by its task definition are resident and complete on the master CPU. A ready task may be transmitted by the master CPU to a slave CPU 650. Typically, the actual data elements will not be transmitted at this time when the slave CPUs process the tasks during idle processing time. When the slave CPU is idle, it accesses the appropriate data elements 636 identified by the task definition 638 from the master CPU. If there are fewer data elements from one of the two databases, the remaining data elements from the more numerous of the two are continuously sent to the master CPU, followed by all task definitions for tasks which are now otherwise complete.

Figure 7:
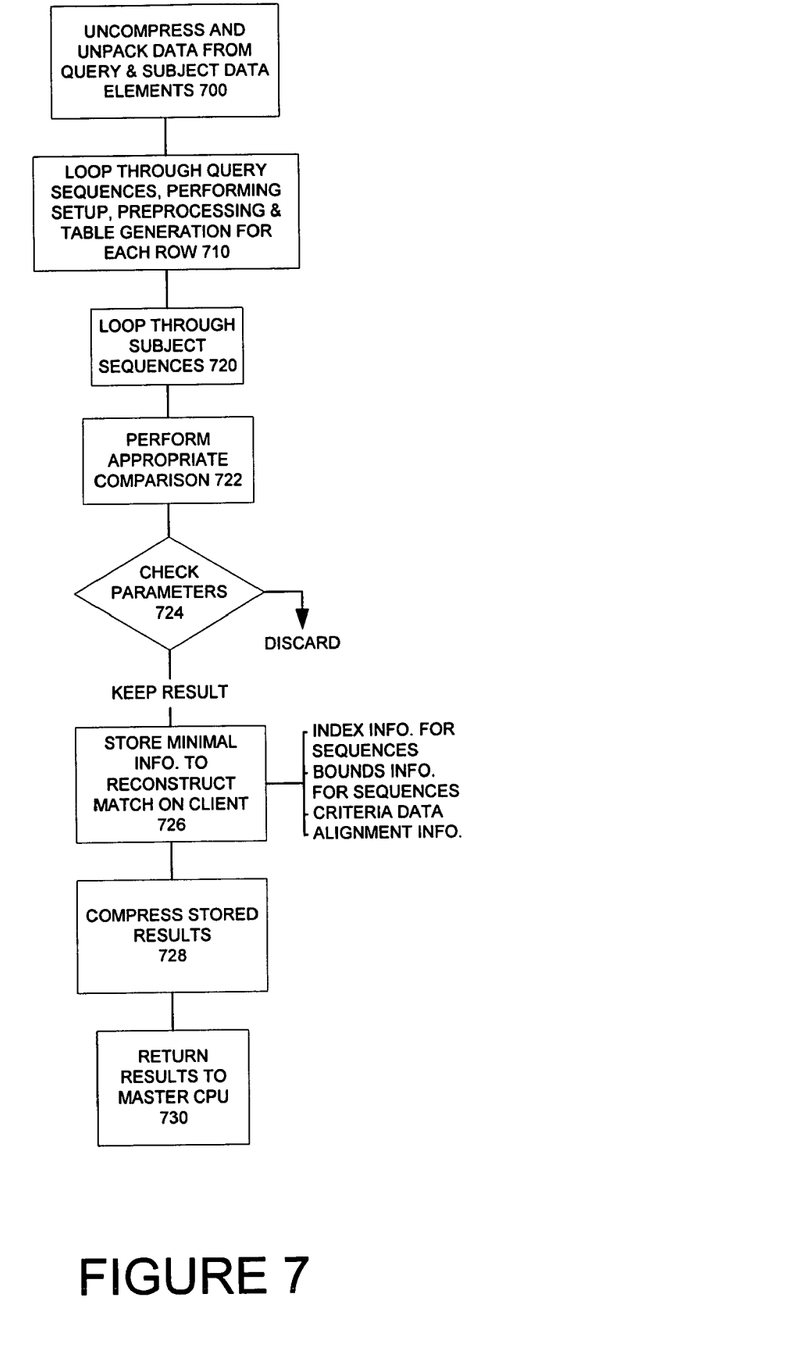
FIG. 7 illustrates a flow chart of a typical slave CPU process in accordance with the present invention.

The tasks are then performed on slave CPUs 660 using the software program embodied in transmitted executable element. As illustrated in FIG. 7, performance of the task on the slave CPU involves uncompressing and unpacking the data from the query and subject data elements 700. The executable loops through the query sequences from the query data element, performing setup, preprocessing, and table generation for each row of comparisons 710, as necessary for the given comparison algorithm, e.g. 20-row amino acid table for Smith-Waterman, 6 translated word hit lookup tables for blastx, low-complexity filtering (dust, seg), etc.

For each query sequence, the executable loops through the subject sequences from the subject data element 720 and, for each query and subject sequence pair, performs the comparison 722 of the query and subject sequence with the included sequence comparison algorithm or algorithms contained in the executable. Using the transmitted sequence comparison parameters 724, the algorithm decides to keep or discard each result based on the user-defined significance criteria, also contained in the transmitted sequence comparison parameters. This may include criteria that take into account characteristics of the entire subject and/or query database.

For each result that meets the user-defined significance criteria, a minimal amount of information is stored 725 that will allow the efficient and complete reconstruction of the significant match on the client CPU. This can include index information for query and subject sequences, bounds information for start and stop of pertinent query and subject sub sequences, data that quantify the fulfillment of the significance criteria for the significant match (e.g., Smith-Waterman or BLAST alignment raw scores, bit scores and E( )-values, etc.), an efficiently encoded representation of the alignment between the bounds specified above corresponding to the high-scoring segment pair, and, for BLAST specifically, the seed point and sumset membership for each alignment.

When all query/subject pairs have been compared, the stored results are compressed 728 and returned from the slave CPU to the master CPU 730, and thereby to the client CPU for results processing 680.

After all tasks have been launched from the client to the master (and preferably, but not necessarily while tasks are being performed), the client can begin to generate query report files 670, one for each sequence in the query database. To do this, the client preferably creates directories for each 1000 sequences in the query database, such as a set named Queries.000–999, Queries.1000–1999, etc., creates one file in the appropriate directory for each sequence in the query database, such as a file named 000.query, 001.query, etc., and puts the query data and metadata for each query sequence at the beginning of each file.

As the set of task results is returned from each task to the client CPU, the client CPU processes each set of task results 680. Typically, the client CPU will retrieve the query and subject sequence data and metadata corresponding to the task that the results came from. For each significant result in the task results, it will retrieve (i) the metadata for the subject sequence, (ii) the partial subject sequence data corresponding to the subject bounds of the significant alignment result, and (iii) the other results data as specified above. The client CPU then appends these data to the query results file corresponding to the query sequence.

When all the task results have been returned from a "row" of tasks, each query file corresponding to query sequences from that row of tasks will contain all information necessary to reproduce a report identical to the BLAST report generated by blastall (and a BLAST-like report for Smith-Waterman). For each complete row of tasks, the query sequence and metadata is retrieved for each query result file, significant results are sorted each query result file by expectation value (taking the sum-set expectation value into account for results that are part of a sum-set—BLAST only), identical/redundant results are removed for each query result file due to overlapping of data elements/sequences, and text output is generated for each query sequence 690 identical to the output generated by a blastall run of the query sequence against the subject database.

When all results from all rows of tasks have been processed, all results may be concatenated 699 together automatically (or manually, if desired) to produce a text results file identical to the output of a single blastall run of the query database vs. the subject database.

What is claimed is:

1. A method of comparing a query dataset N with a subject dataset M, comprising:
   dividing said query dataset N into $n_N$ data elements having a size within a specified range;
   dividing said subject dataset M into $n_M$ data elements having a size within said specified range;
   determining a number of tasks for an entire comparison of datasets N and M as $n_N \times n_M$;
   sending all data elements and task definitions to a master central processing unit (CPU) of a master-slave distributed computing platform,
   wherein task definitions comprise at least one comparison parameter, at least one executable element capable of performing comparisons, a query data element identification(ID)/descriptor, and a subject data element ID/descriptor, and
   wherein data elements are sent alternately from query and subject data elements;
   sending a task definition for each task from the master CPU to one of a plurality of slave CPUs when all parts of a task definition and data elements referenced by said task definition are available at said master CPU;
   sending data elements referenced by said task definition to said slave CPU;
   performing each task on a slave CPU;
   returning task results for each task to said master CPU; and
   generating and outputting a query results file comprising task results.

2. The method of claim 1, further comprising randomizing sequence order of each dataset if either dataset contains related sequences in a contiguous arrangement.

3. The method of claim 1, further comprising formatting said datasets so as to use exactly the same ambiguity substitutions.

4. The method of claim 1 wherein dividing said datasets into data elements further comprises:
   stripping all metadata from data;
   packing said data into an efficient structure;
   creating an index for said data and packing said index and said data in an uncompressed data structure; and
   compressing said uncompressed data structure into a data element using a redundancy reduction data compression method.

5. The method of claim 1, further comprising sending remaining data elements from a more numerous of said datasets to said master CPU followed by all task definitions for otherwise complete tasks if there are fewer data elements from one dataset.

6. The method of claim 1 wherein performing a task on said slave CPU further comprises:
   uncompressing and unpacking data from said query and subject data elements;
   looping through query sequences from said query data element to perform setup, preprocessing and table generation for each row of comparisons;
   looping through subject sequences from said subject data element and, for each pair of query and subject sequences, performing a comparison using said executable element and finding results based on said at least one comparison parameter; and
   storing minimal information that will allow reconstruction of said result.

7. The method of claim 6 wherein storing said minimal information comprises:
   storing index information for said query and said subject sequence;
   storing bounds information for start and stop of said query and subject sub sequences;
   storing data that quantify fulfillment of significance criteria for a significant match; and
   storing an efficiently encoded representation of alignment between said bounds corresponding to a high-scoring segment pair.

8. The method of claim 7, further comprising storing a seed point and sum-set membership for each alignment for Basic Local Alignment Search Tool (BLAST).

9. The method of claim 7, further comprising storing task results in a task result file, said file including query and subject sequence data and metadata corresponding to the task that the results came from, metadata for the subject sequence, the partial subject sequence data corresponding to the subject bounds of the significant alignment result, and any other results data for each result in the task results.

10. The method of claim 9, further comprising generating a BLAST report for each query data element.

11. The method of claim 10, further comprising concatenating results from all BLAST reports to produce a text file identical to a blastall run of said query and subject datasets.

12. The method of claim 1 wherein said datasets are selected from the group consisting of genomic and proteomic databases.

13. A system for comparing a query dataset N with a subject dataset M, comprising:
   a master central processing unit (CPU) of a master-slave distributed computing platform;
   a plurality of slave CPUs capable of communication with said master CPU; and
   a client CPU with instructions for:
      dividing said query dataset N into $n_N$ data elements having a size within a specified range;
      dividing said subject dataset M into $n_M$ data elements having a size within said specified range;
      determining a number of tasks for an entire comparison of datasets N and M as $n_N \times n_M$;
      sending all data elements and task definitions to said master CPU of a master-slave distributed computing platform,
      wherein task definitions comprise at least one comparison parameter, at least one executable element capable of performing comparisons, a query data element identification (ID)/descriptor, and a subject data element ID/descriptor, and
      wherein data elements are sent alternately from query and subject data elements;
   said master CPU comprising instructions for:
      sending a task definition for each task to one of said plurality of slave CPUs when all parts of a task definition and data elements referenced by said task definition are available at said master CPU; and
      sending data elements referenced by said task definition to said slave CPU; and
   said slave CPUs including instructions for:
   performing each task;
   returning task results for each task to said master CPU; and
   generating and outputting a query results file comprising task results.

14. The system of claim 13, further comprising means for randomizing sequence order of each dataset if either dataset contains related sequences in a contiguous arrangement.

15. The system of claim 13, further comprising means for formatting said datasets so as to use exactly the same ambiguity substitutions.

16. The system of claim 13, wherein said instructions for dividing said datasets into data elements further comprises instructions for:
   stripping all metadata from data;
   packing said data into an efficient structure;
   creating an index for said data and packing said index and said data in an uncompressed data structure; and
   compressing said uncompressed data structure into a data element using a redundancy reduction data compression method.

17. The system of claim 13, further comprising instructions for sending remaining data elements from a more numerous of said datasets to said master CPU followed by all task definitions for otherwise complete tasks if there are fewer data elements from one dataset.

18. The system of claim 13, wherein instructions for performing a task on said slave CPU further comprises instructions for:
   uncompressing and unpacking data from said query and subject data elements;
   looping through query sequences from said query data element to perform setup, preprocessing and table generation for each row of comparisons;
   looping through subject sequences from said subject data element and, for each pair of query and subject sequences, performing a comparison using said executable element and finding results based on said at least one comparison parameter; and
   storing minimal information that will allow reconstruction of said result.

19. The system of claim 18, wherein said instructions for storing said minimal information comprises instructions for:
   storing index information for said query and said subject sequence;
   storing bounds information for start and stop of said query and subject sub sequences;
   storing data that quantify fulfillment of significance criteria for a significant match; and
   storing an efficiently encoded representation of alignment between said bounds corresponding to a high-scoring segment pair.

20. The system of claim 19, further comprising instructions for storing task results in a task result file, said file including query and subject sequence data and metadata corresponding to the task that the results came from, metadata for the subject sequence, the partial subject sequence data corresponding to the subject bounds of the significant alignment result, and any other results data for each result in the task results.

21. The system of claim 20, further comprising instructions for generating a Basic Local Alignment Search Tool (BLAST) report for each query data element.

22. The system of claim 21, further comprising means for concatenating results from all BLAST reports to produce a text file identical to a blastall run of said query and subject datasets.

23. The system of claim 13, wherein said datasets are selected from the group consisting of genomic and proteomic databases.

* * * * *